US00PP24156P2

(12) United States Plant Patent
van Lankveld

(10) Patent No.: US PP24,156 P2
(45) Date of Patent: Jan. 14, 2014

(54) *EUONYMUS* PLANT NAMED 'LANKVELD03'

(50) Latin Name: *Euonymus japonicus*
Varietal Denomination: Lankveld03

(76) Inventor: Martinus T. M. van Lankveld, Elsendorp (NL)

( * ) Notice: Subject to any disclaimer, the term of this patent is extended or adjusted under 35 U.S.C. 154(b) by 11 days.

(21) Appl. No.: 13/507,814

(22) Filed: Jul. 30, 2012

(51) Int. Cl.
*A01H 5/00* (2006.01)

(52) U.S. Cl.
USPC ..... Plt./246

(58) Field of Classification Search
USPC ..... Plt./246
See application file for complete search history.

*Primary Examiner* — Kent L Bell
(74) *Attorney, Agent, or Firm* — Penny J. Aguirre

(57) ABSTRACT

A new cultivar of *Euonymus florida*, 'Lankveld03', characterized by its foliage that has new growth that is white in color and gradually becoming dark green with age, its an upright plant habit, and its dense basal branching.

2 Drawing Sheets

Botanical classification: *Euonymus japonicus*.
Variety denomination: 'Lankveld03'.

BACKGROUND OF THE INVENTION

The present invention relates to a new and distinct cultivar of *Euonymus japonicus* and will be referred to hereafter by its cultivar name, 'Lankveld03'. 'Lankveld03' is a new cultivar of evergreen shrub grown for use as an ornamental landscape plant.

The Inventor discovered the new cultivar in summer of 2004 as a naturally occurring branch mutation of *Euonymus* 'Fransien' (not patented) that was growing in a container at his nursery in Elsendorp, The Netherlands.

Asexual reproduction of the new cultivar was first accomplished by the Inventor using softwood stem cuttings in summer of 2006 in Elsendorp, The Netherlands. The characteristics of this cultivar have been determined to be stable and are reproduced true to type in successive generations.

SUMMARY OF THE INVENTION

The following traits have been repeatedly observed and represent the characteristics of the new cultivar as grown outdoors in a trial plot in Elsendorp, The Netherlands. These attributes in combination distinguish 'Lankveld03' as a unique cultivar of *Euonymus*.

1. 'Lankveld03' exhibits foliage that has new growth that is white in color and gradually becomes dark green with age.
2. 'Lankveld03' exhibits an upright plant habit.
3. 'Lankveld03' exhibits dense basal branching.

The parent, 'Fransien', differs from 'Lankveld03' in having new growth that is variegated with green centers and white margins. 'Lankveld03' can be most closely compared to other cultivars that have new growth with unique coloration. 'Heespierrolino' (U.S. Plant Pat. No. 13,852) and 'Hees Pierrolino' (not patented) differ from 'Lankveld03' in having white new growth that becomes speckled with green and white. 'Happiness' (U.S. Plant Pat. No. 21,823) differs from 'Lankveld03' in having new growth that is yellow-green in color. 'Butterscotch' (not patented) differs from 'Lankveld03' in having new growth that is lemon yellow in color.

BRIEF DESCRIPTION OF THE DRAWING

The accompanying colored photographs illustrate the overall appearance and distinct characteristics of 2 year-old plants of the new cultivar as grown outdoors in 2-liter containers in full sun in Elsendorp, The Netherlands.

The photograph in FIG. 1 provides an overall view of the growth habit of 'Lankveld03'.

Figure 1:
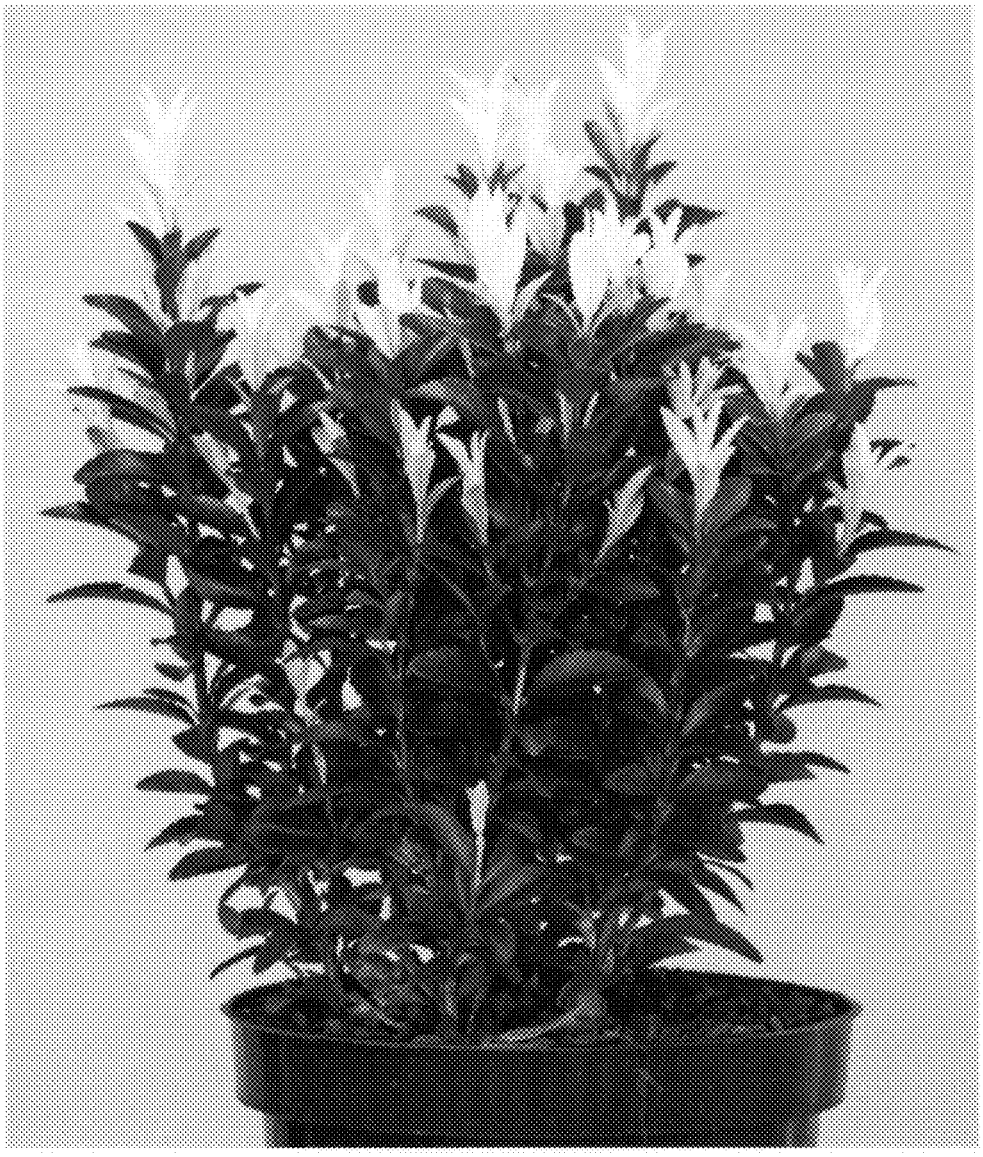
Figure 2:
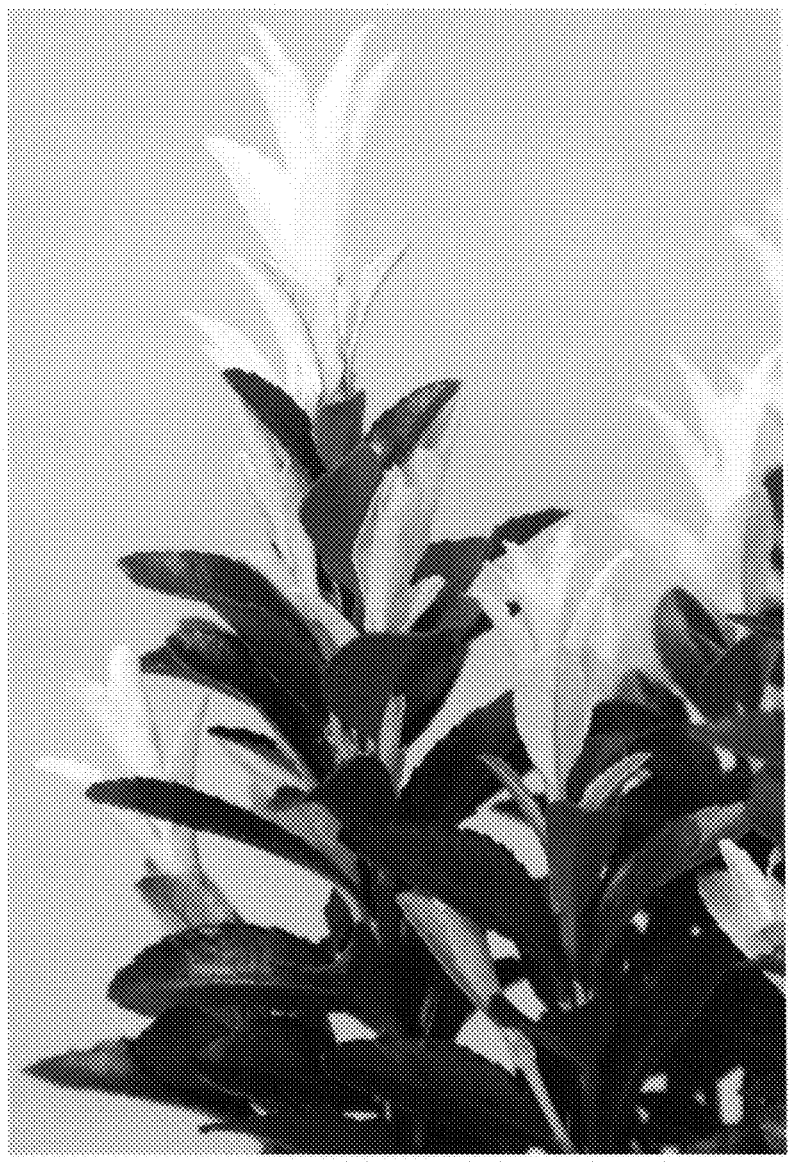

The photograph in FIG. 2 provides a close-up view of the foliage of 'Lankveld03'.

The colors in the photograph may differ slightly from the color values cited in the detailed botanical description, which accurately describe the colors of the new *Euonymus*.

DETAILED BOTANICAL DESCRIPTION

The following is a detailed description of 2 year-old plants of the new cultivar as grown outdoors in 2-liter containers in full sun in Elsendorp, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Flowering has not been observed on the new cultivar.

*Plant type.*—Perennial evergreen shrub.

*Plant habit.*—Upright, dense basal branching.

*Plant size.*—Reaches about 27.2 cm in height and 21.8 cm in width and up to 50 cm in height and 35 cm in width in the landscape.

*Hardiness.*—At least hardy to U.S.D.A. Zone 7.

*Environmental stress.*—Highly tolerant to wind and rain.

*Diseases and pests.*—Not more susceptible to pests and diseases than other *Euonymus japonicus* varieties.

*Root description.*—Fibrous, moderately dense.
*Growth rate.*—Slow to moderate.

Stem description:
*Shape.*—Round.
*Stem color.*—New growth; between 137A and N137A, mature wood; 199D.
*Stem size.*—An average of 19.7 cm in length and 2.5 mm in diameter.
*Stem surface.*—Smooth and glossy.
*Stem aspect.*—Upright.
*Stem strength.*—Strong.
*Branching.*—Basal branching, an average of 20 lateral branches.

Foliage description:
*Leaf shape.*—Ovate to elliptic.
*Leaf division.*—Simple.
*Leaf base.*—Short attenuate.
*Leaf apex.*—Obtuse.
*Leaf fragrance.*—None.
*Leaf venation.*—Pinnate, color of upper and lower surfaces; 138A.
*Leaf margins.*—Crenate.
*Leaf arrangement.*—Opposite.
*Leaf attachment.*—Petiolate.
*Leaf surface.*—Upper surface; smooth and very glossy, lower surface; smooth and moderately glossy.
*Leaf internode length.*—An average of 1.1 cm.
*Leaf size.*—An average of 3.0 cm in length and 1.4 cm in width.
*Leaf quantity.*—An average of 36 per stem.
*Leaf color.*—Immature upper surface; 155A, immature lower surface; between 155A and 157D, mature and fall upper surface; between N137A and 147A, mature and fall lower surface; between 137A and 147B.
*Petioles.*—About 3 mm in length and 1 mm in width, color; 138A.
*Stipules.*—None.

Inflorescence/fruit description: No flowers or fruit have been observed to date.

It is claimed:

1. A new and distinct cultivar of *Euonymus* plant named 'Lankveld03' as herein illustrated and described.

* * * * *